United States Patent [19]
Kutner et al.

[11] Patent Number: 5,871,702
[45] Date of Patent: Feb. 16, 1999

[54] METHODS AND APPARATUS FOR STERILIZING OBJECTS

[75] Inventors: Barry S. Kutner, Wilton; Daniel A. Latowicki, Newtown, both of Conn.

[73] Assignee: Flexiclave, Inc., Briarcliff, N.Y.

[21] Appl. No.: 857,329

[22] Filed: Mar. 25, 1992

Related U.S. Application Data

[63] Continuation-in-part of Ser. No. 692,736, Apr. 29, 1991, Pat. No. 5,413,757, which is a continuation of Ser. No. 274,768, Nov. 22, 1988, Pat. No. 5,039,495, which is a continuation-in-part of Ser. No. 184,246, Apr. 21, 1988, Pat. No. 5,019,344.

[51] Int. Cl.$^6$ ........................................................ A61L 2/12
[52] U.S. Cl. ............................. 422/299; 422/21; 422/22; 422/28; 422/33; 422/294; 422/305
[58] Field of Search ................................. 422/21, 22, 28, 422/32, 33, 294, 299, 305; 219/10.55 R, 10.55 E, 10.55 D, 10.55 M

[56] References Cited

U.S. PATENT DOCUMENTS

| | | | |
|---|---|---|---|
| 3,215,539 | 11/1965 | Landy | 99/221 |
| 3,219,460 | 11/1965 | Brown | 99/192 |
| 3,261,140 | 7/1966 | Long et al. . | |
| 3,490,580 | 1/1970 | Brumfield et al. | 219/10.55 E |
| 3,494,722 | 2/1970 | Gray | 21/54 |
| 3,494,724 | 2/1970 | Gray | 21/54 |
| 3,494,726 | 2/1970 | Barasch . | |
| 3,551,090 | 12/1970 | Brumfield et al. . | |
| 3,615,713 | 10/1971 | Stevenson | 99/171 |
| 3,676,058 | 7/1972 | Gray | 21/54 |
| 3,753,651 | 8/1973 | Boucher . | |
| 3,965,323 | 6/1976 | Forker, Jr. et al. | 219/10.55 E |
| 3,974,353 | 8/1976 | Goltsos | 219/10.55 E |
| 4,013,798 | 3/1977 | Goltsos | 219/10.55 E |
| 4,015,085 | 3/1977 | Woods . | |
| 4,122,324 | 10/1978 | Falk | 219/10.55 E |
| 4,132,811 | 1/1979 | Standing et al. | 219/10.55 E |
| 4,190,757 | 2/1980 | Turpin et al. . | |
| 4,196,331 | 4/1980 | Levickis et al. . | |
| 4,204,105 | 5/1980 | Levickis et al. . | |
| 4,228,334 | 10/1980 | Clark et al. . | |
| 4,283,427 | 8/1981 | Winters et al. . | |
| 4,400,357 | 8/1983 | Hohmann . | |
| 4,514,497 | 4/1985 | Kit et al. . | |
| 4,808,782 | 2/1989 | Nakagawa et al. | 219/10.55 |
| 4,865,921 | 9/1989 | Hollenberg et al. . | |
| 4,878,765 | 11/1989 | Watkins et al. . | |
| 5,019,344 | 5/1991 | Kutner et al. | 422/21 |
| 5,019,359 | 5/1991 | Kutner et al. | 422/21 |
| 5,039,495 | 8/1991 | Kutner et al. | 422/299 |

FOREIGN PATENT DOCUMENTS

| | | |
|---|---|---|
| 3505571 | 8/1986 | Germany . |
| 3149053 | 6/1991 | Japan ................. A61L 2/12 |
| WO804133 | 3/1980 | WIPO . |

Primary Examiner—Timothy McMahon
Attorney, Agent, or Firm—Steinberg & Raskin, P P.C.

[57] ABSTRACT

An arrangement for sterilizing objects in which a quantity of liquid and one or more objects to be sterilized are introduced into a pouch formed of flexible sheet material at least partially transparent to microwave radiation whereupon the pouch is sealed to form a gas-tight assembly. The gas-tight assembly is situated in an inner rigid cavity of an enclosure which is at least partially formed of material that is substantially transparent to microwave radiation. The enclosure is irradiated with microwave radiation which passes into the cavity and then into the gas-tight pouch assembly situated therein to vaporize the liquid to produce an atmosphere of hot vapor under pressure in the pouch. The pouch expands under pressure until the sheet material of which it is formed presses against the rigid inner surfaces of the enclosure cavity. At least a part of the gas-tight pouch assembly may be surrounded with microwave radiation shielding which divides the interior of the pouch into shielded and unshielded interior portions, the object to be sterilized being situated in the shielded pouch portion while the liquid to be vaporized is situated in the second unshielded pouch portion.

28 Claims, 6 Drawing Sheets

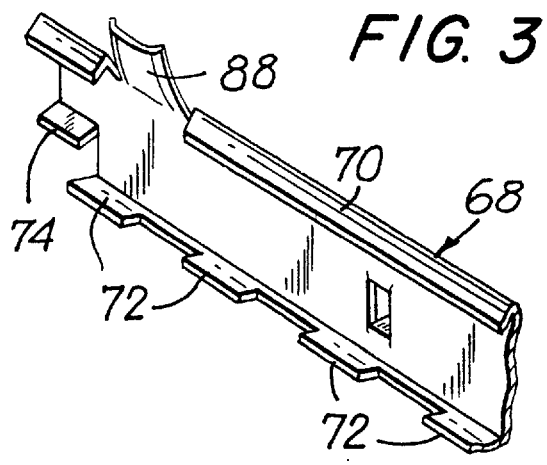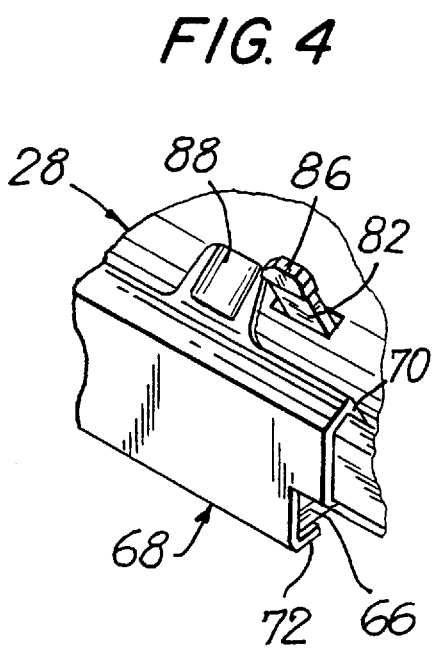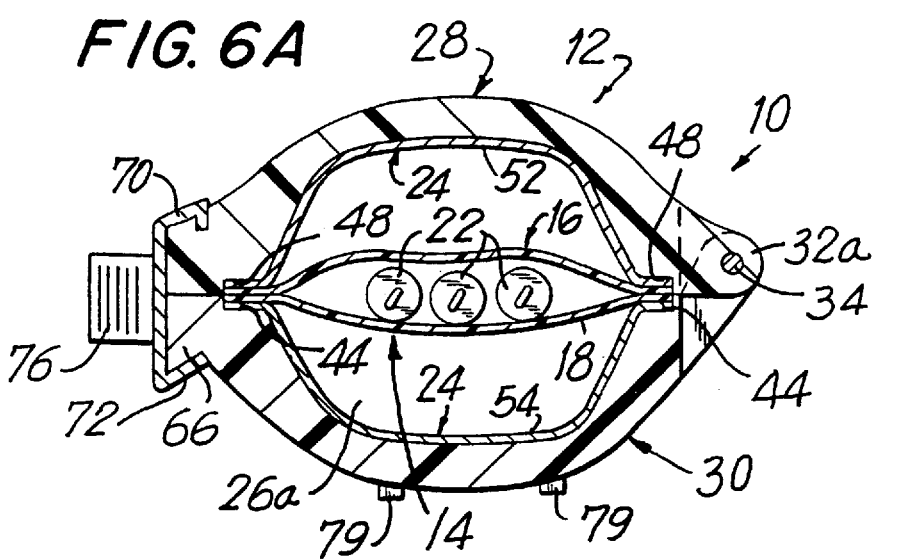

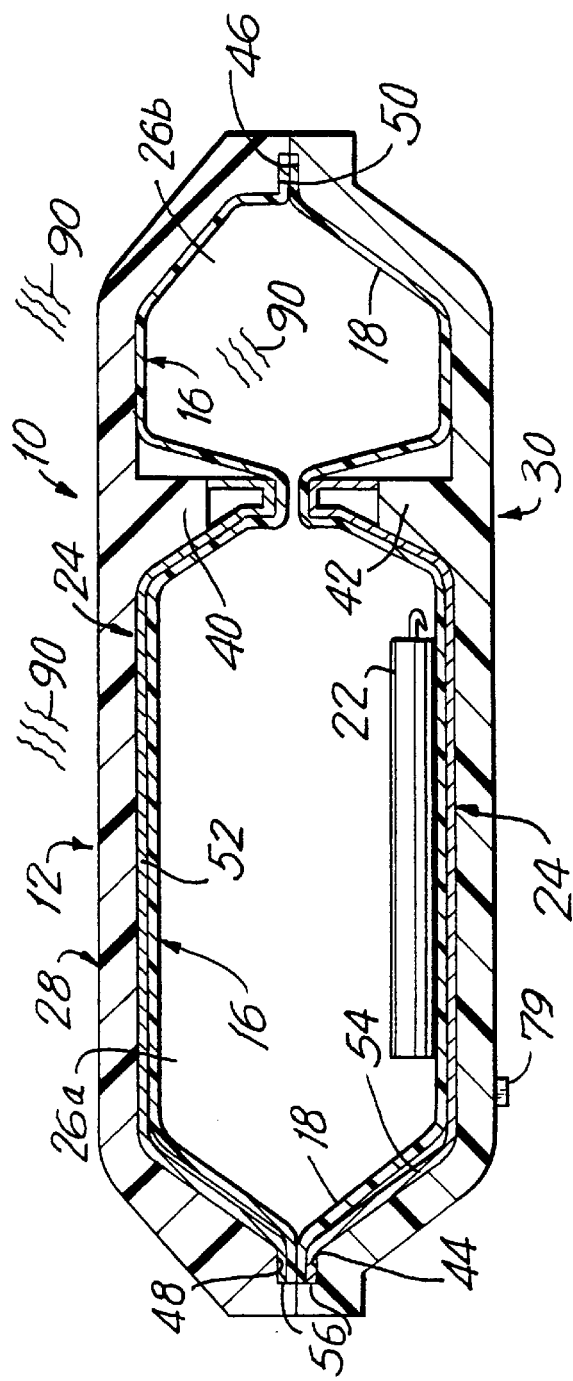
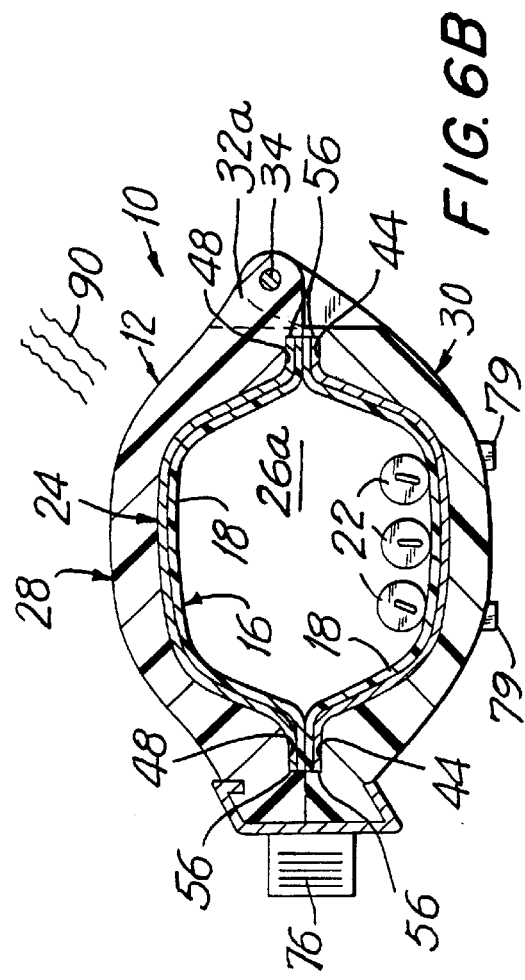
FIG. 5B
FIG. 6B

METHODS AND APPARATUS FOR STERILIZING OBJECTS

This is a continuation-in-part of application Ser. No. 07/692,736 filed Apr. 29, 1991 now U.S. Pat. No. 5,413,757, which is a continuation of Ser. No. 07/274,768 filed Nov. 22, 1988, now U.S. Pat. No. 5,039,495, which is a continuation-in-part of application Ser. No. 07/184,246, filed Apr. 21, 1988, now U.S. Pat. No. 5,019,344.

BACKGROUND OF THE INVENTION

This invention relates generally to methods and apparatus for disinfecting or sterilizing objects, and more particularly, to methods and apparatus for disinfecting or sterilizing objects, such as dental and medical instruments. As used hereinbelow, the terms "sterilizing", "sterilization", and the like will be used in their broadest sense and should be understood to mean the killing of bacteria and spores, as well as the killing of bacteria to the extent necessary for a particular purpose, and may include the process of "disinfection."

The need for effective sterilization of dental instruments, such as dental handpieces, is more important today than ever before due to the realization of the significant potential for infection via dental procedures and the increase in the rate of transmission of serious diseases by blood and saliva. However, from a practical viewpoint, not only must the sterilization procedure be effective, it must also be rapid, i.e., have a short turn-around or cycle time. Thus, it will be understood that the quantity of any one instrument that a practitioner or institution must purchase and have available for use will depend on the frequency of treatments requiring that instrument and on the turn-around time required to sterilize the instrument. In the case of dental handpieces, which generally are required for most treatments performed in the dental operatory, an extended sterilization cycle means that a larger inventory of available handpieces must be maintained. The high cost of dental handpieces, on the other hand, often limits the number of available handpieces, which in turn may result in hasty and therefore ineffective attempts at, or even dispensing with, lengthy sterilization procedures. This of course is unacceptable.

Heat sterilization methods, such as steam heat (autoclave), dry heat, and chemical vapor, are generally preferred over cold immersion methods, which are generally not effective unless glutaraldehyde is used and the instrument is immersed for 7–10 hours. Chemical vapor sterilization has the advantages of minimal corrosion of burs and other sharp instruments (steam sterilization or immersion in most liquid sterilents produces dullness and rusting) and a cycle time which is relatively short compared to cold sterilization techniques.

One type of chemical vapor sterilizing arrangement which is in commercial use (available from MDT Corporation of Gardena, California under the designation Harvey Chemiclave) comprises apparatus which uses moderate heat (about 270° F.), pressure (about 20 psi) and a special solution composed primarily of 3A alcohol (about 80%) and water (about 9%) with small amounts of acetone, ketone and formaldehyde. The cycle time is about 20 minutes after proper pressure is reached. The length of time required to reach pressure depends on the size of the load. On the other hand, the purchase price of this arrangement is higher than steam and dry heat processors. Additional drawbacks are that relatively large quantities of sterilizing solution are required, and odor and minor irritation of eyes, nose and throat from chemical vapors often accompanies use, the process chamber must be cleaned on a frequent basis, the instruments should be wrapped to prevent recontamination, and the simultaneous sterilization of a plurality of instruments results in the possibility of cross contamination. Moreover, the sterilization cycle time, although less than the time required for the sterilization by solution immersion, is still relatively long, essentially because of the relatively large chamber volume.

U.S. Pat. No. 4,400,357 issued Aug. 23, 1983 to Hohmann, discloses an arrangement for chemical vapor sterilization of articles, such as dental handpieces, which would appear to overcome some of the above-mentioned problems. The patent discloses an arrangement in which the article to be sterilized is situated in an enlarged portion of a rigid vessel. A liquid reaction agent is charged into a narrow portion of the vessel which is in communication with the enlarged article-containing vessel portion. The liquid reaction agent is heated to produce a vapor which flows into the first vessel portion to sterilize the article. The first vessel portion may be designed to accept only a single article in which case the amount of liquid reaction agent required to generate the vapor is relatively small which in turn reduces the heating time required for vaporization and the overall sterilization cycle time. The patent suggests that the means for heating the liquid reaction agent may comprise a microwave radiator. In such a case, the vessel is situated such that only the narrow liquid-containing vessel portion is positioned in the microwave radiation field while the article to be sterilized is situated outside the radiation field which, the patent notes, avoids the formation of spark gaps at border surfaces and seams of the article which cause surface destruction. Although possibly reducing the time required for sterilization, the arrangement proposed in the patent has various drawbacks which have apparently prevented adoption and commercialization of this arrangement. For example, it requires a complicated, specially designed microwave generator adapted for positioning the vessel with only the liquid reaction agent-containing portion in the radiation field of the microwave generator with the article-containing vessel portion outside the radiation field. It requires a specially designed rigid pressure vessel which either must be cleaned after each use to avoid cross-contamination or discarded at significant expense.

A discussion of the sterilization of articles, such as dental instruments, by microwave radiation is set forth in U.S. Pat. No. 3,753,651 issued Aug. 21, 1973 to Boucher. Briefly, it is noted that sterilization by microwave radiation is due to both thermal effects, such as microwave induced heat, and non-thermal effects, which the patent suggests may affect a metabolic system distinct from that of thermal energy. It is disclosed that improved surface sterilization results are obtained when the articles are subjected to microwave radiation while situated in a humid atmosphere, i.e., an atmosphere having a relative humidity of at least 50% or super-saturated with water or saline solution. To this end, the articles to be sterilized are placed on trays which are situated in a rigid, microwave-transparent container having a known volume, along with a quantity of water or saline solution determined by the container volume so as to be sufficient when vaporized to increase the humidity of the atmosphere within the container to the desired value. After placing the articles to be sterilized and the water or saline solution into the container, the container is sealed with a lid and then placed within the cavity of a microwave generator and subjected to microwave radiation. The electromagnetic energy penetrates through the container walls to evaporate the water or saline solution to produce the desired humidity, and at the same time, proceeds to sterilize the surface of the article by the thermal and non-thermal effects discussed above. It is indicated that this procedure results in reduced cycle time for effective sterilization compared to dry heat or steam sterilizing methods and that the localized arcing (sparking) which usually occurs when metallic objects are irradiated by microwave radiation is practically eliminated in the moist atmosphere.

The patent also points out that the container can be filled with any gas to constitute the atmosphere to be humidified. For example, it is suggested that a gas or vapor sterilant can be introduced into the container through valves provided in the container walls to take advantage of their chemical sterilizing effects, although care should be taken to avoid heating the article being sterilized to a point where it reaches the ignition or explosion point of the gas, The arrangement proposed in U.S. Pat. No. 3,753,651 has drawbacks which have apparently prevented it from being adopted on a practical basis. For example, as noted in the above-discussed U.S. Pat. No. 4,400,357, only surface sterilization is achieved by microwave irradiation and microorganisms present on surfaces located within the seams and crevices of the article will not be killed, especially if blood and salivary protein are deposited on those surfaces. This is true regardless of whether the container is initially filled with a gas sterilant as suggested in the patent. The procedure requires a specially designed gas-tight rigid container having a known, fixed volume. The container must be sterilized after each use or discarded, in which case considerable expense is incurred especially where valves are provided in the container walls as discussed above. To provide a truly gas-tight condition, it is necessary to use materials, such as for gaskets and the like, which are not entirely transparent to microwaves. Moveover, the relatively large volume of the container which is necessary to accommodate the articles to be sterilized in turn requires a relatively large volume of water or saline solution to achieve the desired humidity. This results in an increase in the time required for the evaporation of the water or saline solution thereby increasing the overall sterilization cycle time. Furthermore, it is not thought that the arrangement described in this patent will avoid the problem of arcing or sparking.

Applicants have developed new and improved methods and apparatus for sterilizing objects which overcome many of the drawbacks of the prior art arrangements discussed above. In particular, methods and apparatus for sterilizing objects are disclosed in applicants' prior U.S. Pat. Nos. 5,019,344 issued May 28, 1991 and 5,039,495 issued Aug. 13, 1991, the descriptions of which are hereby incorporated herein in their entirety. These patents describe arrangements in which an object to be sterilized and a quantity of liquid are introduced into a pouch formed of flexible vapor-impermeable sheet material whereupon the pouch is sealed to form a gas-tight assembly. The liquid is introduced into the pouch in a quantity sufficient to create an over-pressure within the pouch when it is vaporized which expands the pouch, whereupon the object becomes sterilized under the effect of the hot vapor under pressure. The liquid within the pouch may be vaporized by irradiating the gas-tight assembly with microwave radiation in which case the object being sterilized is preferably surrounded by shielding which presents a barrier to the transmission of microwave radiation to thereby avoid arcing or sparking. The arrangements developed by the applicants which are disclosed in the above-mentioned patents are advantageous in that the time required for a sterilizing cycle is substantially reduced relative to prior techniques, a visual indication that the process is proceeding is provided by virtue of the expanding pouch, the arrangements are inexpensive in manufacture and use, and they allow the subsequent handling and storage of the sterilized object without the danger of recontamination. The arrangements may be used for sterilizing a wide variety of objects including medical and dental instruments, medical waste material, contact lenses, and the like.

SUMMARY OF THE INVENTION

A general object of the present invention is to provide new and improved methods and apparatus for sterilizing objects, such as dental and medical instruments.

Another object of the present invention is to provide new and improved methods and apparatus for sterilizing objects by hot vapor under pressure which require less time and which are simpler in construction and more economical in use then prior art arrangements.

Still another object of the present invention is to provide additional improvements in the methods and apparatus for sterilizing objects described in applicants' patents mentioned above.

Briefly, in accordance with one aspect of the present invention, these and other objects are attained by providing an arrangement in which a quantity of liquid and one or more objects to be sterilized are introduced into a pouch formed of flexible sheet material at least partially transparent to microwave radiation, the quantity of liquid being sufficient so that when the pouch is sealed to form a gas-tight assembly and the liquid is vaporized by irradiating it with microwave radiation, an overpressure is created within the pouch which causes the pouch to expand. The gas-tight assembly is thereupon situated in an inner rigid cavity of an enclosure which is at least partially formed of material that is substantially transparent to microwave radiation. The enclosure is irradiated with microwave radiation which passes into the cavity and then into the gas-tight assembly situated therein to vaporize the liquid thereby producing an atmosphere of hot vapor under pressure in the pouch. The pouch expands under pressure until the sheet material of which it is formed presses against the rigid inner surfaces of the enclosure that define the enclosure cavity whereupon further expansion of the pouch is prevented while the shape of the pouch substantially conforms to the shape of the cavity. The enclosure may be adapted with means for providing a visual indication that the sterilizing process is proceeding.

According to another aspect of the invention, prior to irradiation, at least a part of the gas-tight assembly is surrounded with microwave radiation shielding means which divide the interior of the pouch into a first interior portion which will be substantially free of microwave radiation during the irradiation step, and a second interior portion which will be exposed to the microwave radiation during irradiation. The at least one object to be sterilized is situated in the first shielded interior pouch portion while the liquid to be vaporized is situated in the second unshielded interior portion of the pouch.

The shielding means may take the form of one or more shield members which are themselves situated within, or may form, the interior cavity of the enclosure, to surround at least a part of the gas-tight pouch assembly which is also situated in the enclosure cavity.

The method and apparatus of the invention provide all of the advantages of the basic arrangements disclosed in applicants' U.S. Pat. Nos. 5,019,344 and 5,039,495. Moreover, higher temperatures and pressures may be obtained using the arrangement of the present invention and therefore cycle times are reduced still further. The invention facilitates handling and set-up, increases reliability and improves safety.

DESCRIPTION OF THE DRAWINGS

A more complete appreciation of the present invention and many of the attendant advantages thereof will be readily understood by reference to the following detailed description when considered in connection with the accompanying drawings in which:

FIG. 3 is a partial perspective view from the rear of a closure slide forming a part of the enclosure of FIG. 1;

FIG. 4 is a partial perspective view of the enclosure of FIG. 1 illustrating detent-indicator means for locking the closure slide in its locked position during operation and for visually indicating that the sterilizing process is proceeding;

FIG. 5B is a view similar to FIG. 5A, during irradiation;

FIG. 6A is a section view taken along line 6—6 of FIG. 1, prior to irradiation;

FIG. 6B is a view similar to FIG. 6A, during irradiation;

DETAILED DESCRIPTION OF THE PREFERRED EMBODIMENTS

Figure 1:
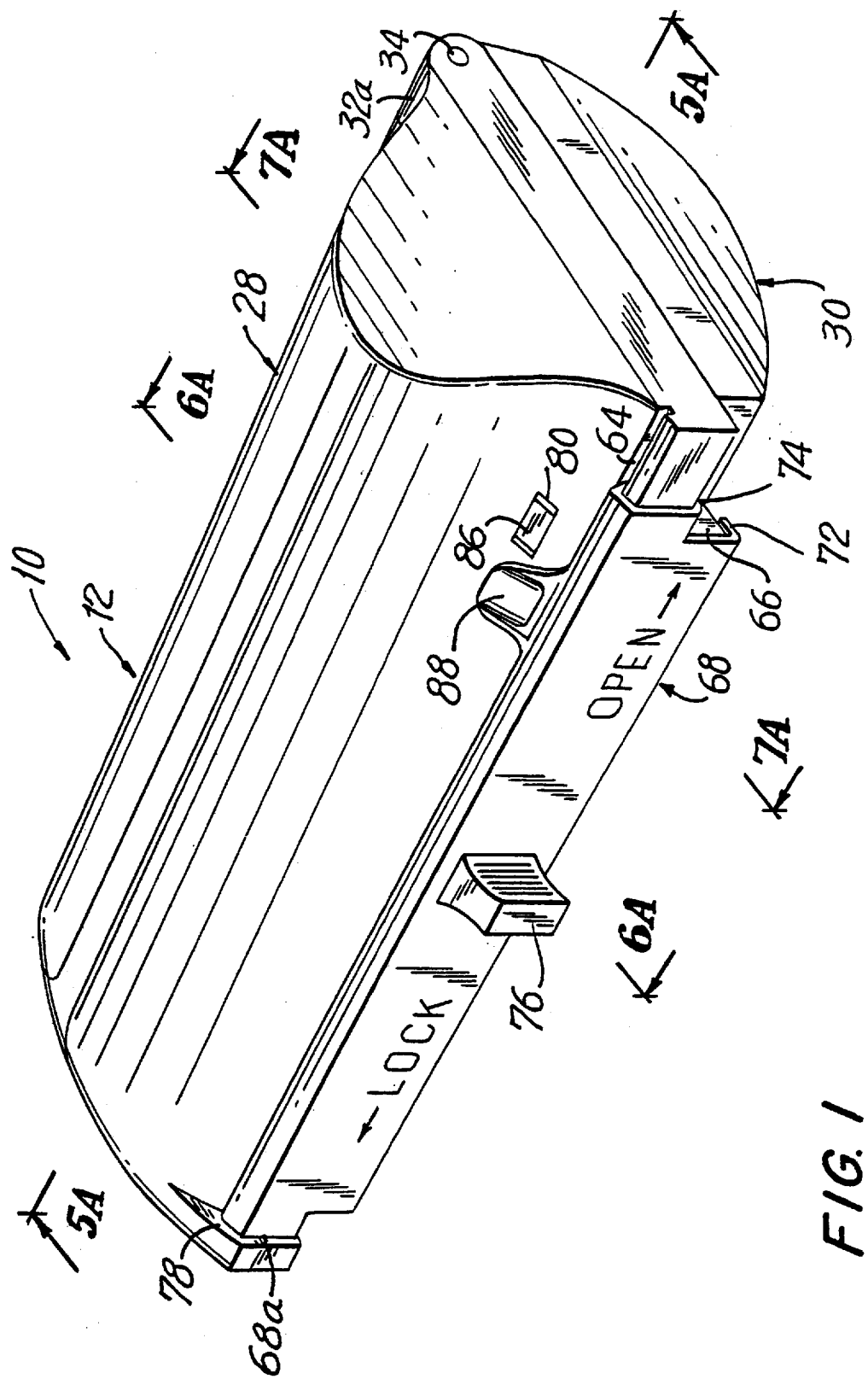
FIG. 1 is a perspective view of an enclosure in its closed condition in accordance with the invention.
Figure 2:
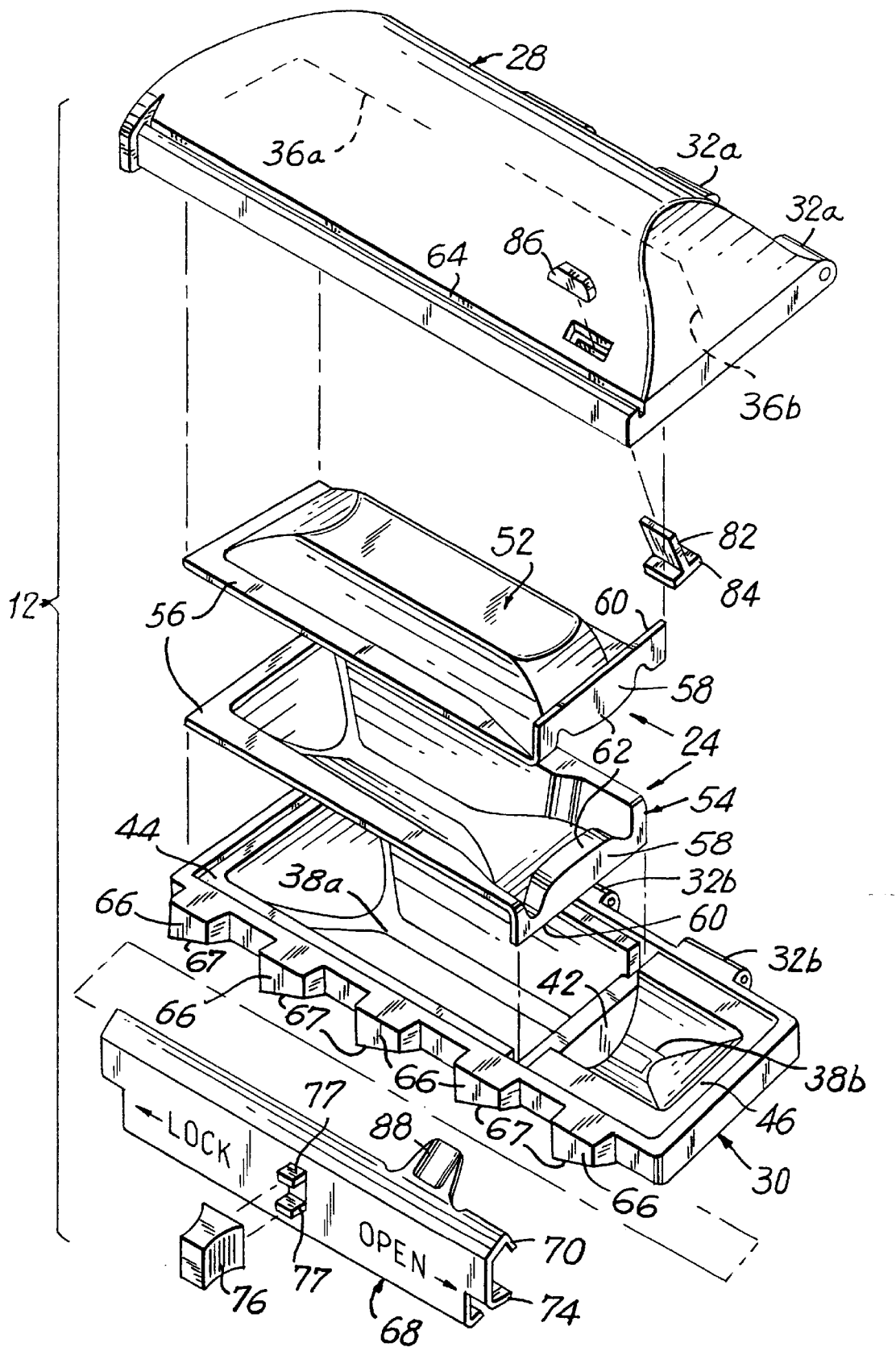
FIG. 2 is an exploded perspective view of the enclosure shown in FIG. 1, and illustrating shielding means received therein.
Figure 5A:
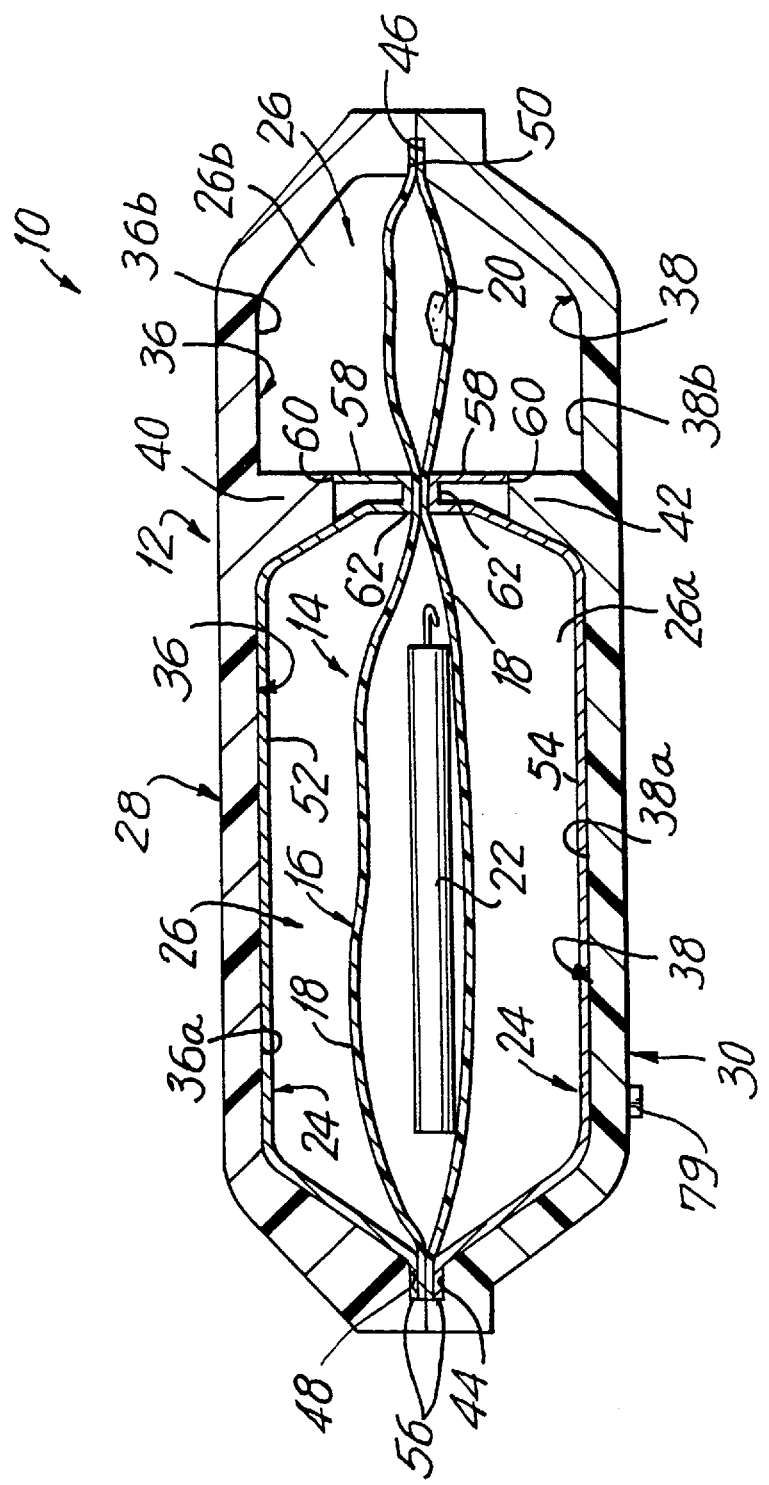
FIG. 5A is a section view taken along line 5—5 of FIG. 1 illustrating the inner cavity of the enclosure and the shielding means and gas-tight pouch assembly containing objects to be sterilized situated within the cavity, prior to irradiation.

Referring now to the drawings wherein like reference characters designate identical or corresponding parts throughout the several views, and more particularly to FIGS. 1, 2 and 5A, apparatus in accordance with the present invention, generally designated 10, comprise an enclosure 12 and a gas-tight assembly 14 (FIG. 5A) including a sealed pouch 16 formed of flexible sheet material 18 and, sealed therein, a quantity of liquid 20 and at least one object 22 to be disinfected. In the illustrated embodiment, enclosure 12 also comprises microwave radiation shield means 24.

The fundamental principles of the arrangement of the present invention are similar to those described in the aforementioned applicants' U.S. Pat. Nos. 5,019,344 and 5,039,495. Generally, referring to FIG. 5A, the pouch 16 is formed of flexible substantially vapor-impermeable sheet material which is at least partially transparent to microwave electromagnetic radiation. For example, the sheet material 18 of pouch 16 may comprise a laminate of polypropylene and polyester film material. Initially, the pouch has a sealable opening (not shown) through which the at least one object 22 to be disinfected is introduced into the pouch interior. The liquid 20 in the illustrated embodiment comprises water but may also comprise other liquid disinfectants or sterilants such, for example, as hydrogen peroxide. The liquid 20 is provided in a quantity sufficient such that when the pouch is sealed and the liquid is vaporized, an overpressure is created within the pouch 20 which will cause it to expand. For example, about 10 ml. of water may be used in a pouch having a volume of about 50 cc. The microwave shielding means 24, as described in greater detail below, are associated with the pouch 16 in a manner such that the interior of the pouch is divided into a first interior portion which is substantially free of microwave radiation during irradiation of the sealed pouch assembly, and a second interior portion which is exposed to the radiation during irradiation. As in the case of the method disclosed in the prior patents, in accordance with the present invention, the at least one object 22 to be sterilized is situated in the first shielded interior portion of the pouch and the liquid 20 is situated in the second unshielded interior pouch portion. The pouch is irradiated with microwave radiation at which time the liquid situated in the unshielded portion of the pouch is irradiated, heated and vaporized. At the same time, however, the at least one object 22 situated in the shielded portion of the pouch is not exposed to the radiation so that sparking or arcing is avoided. An overpressure is created within the pouch through the vaporization of the liquid whereupon the at least one object 22 is sterilized under the effect of the hot vapor under pressure.

The present invention provides improvements in the methods and apparatus disclosed in applicants' prior patents. Referring now to FIGS. 1, 2, and 5A, in accordance with one aspect of the present invention, the enclosure 12 defines an inner cavity 26 (FIG. 5A) in which the gas-tight assembly comprising the pouch 16, liquid 20, and the object or objects 22 to to be disinfected, is received. Enclosure 12 comprises a pair of substantially rectangular-shaped cover members 28, 30 which are hinged to each other along corresponding ones of their long sides by inter-meshing piano hinges 32a, 32b and a pin 34.

Referring to FIGS. 2 and 5A, similarly-shaped depressions 36 and 38 are formed in cover members 28, 30 respectively which together form the inner cavity 26 when the enclosure 12 is in its closed condition. Vertical walls 40 and 42 project a limited distance into each of the respective depressions 36, 38 to divide them into respective sub-depressions 36a, 36b; 38a, 38b. A first horizontal shoulder 44 extends around three sides of the periphery of sub-depression 38a while a second horizontal shoulder 46 extends around three sides of the periphery of sub-depression 38b. Similar shoulders 48 and 50 are formed around corresponding sides of the sub-depressions 36a and 36b in cover member 28. As seen in FIGS. 5A and 5B, when the enclosure 12 is closed with the cover members 28, 30 in the positions shown, sub-depressions 36a and 38a cooperate to define an inner sub-cavity 26a while sub-depressions 36b and 38b cooperate to define an interior sub-cavity 26b which communicates with sub-cavity 26a through the space between walls 40 and 42.

Shield means 24 comprise a pair of shield members 52 and 54 formed of aluminum sheet material. Any other suitable material which is opaque to microwave radiation may be used. The shield members 52 and 54 comprise substantially rectangular, concave members which correspond in shape to the shape of the sub-depressions 36a and 38a respectively so that each fits snugly into to be held within a corresponding sub-depression. Each of the shield members has a horizontal peripheral rim 56 extending around three of its sides which become clamped between corresponding shoulders 44, 48 when enclosure 12 is in its closed condition. The fourth side of each of the shield members 52, 54 is shaped to define a substantially vertical radiation barrier wall 58 which terminates at a straight outer edge 60 that engages the inner surface of the divider walls 40 and 42. The inner boundaries of the radiation barrier walls 58 comprise arcuate surfaces 62 shaped such that the radiation barrier walls 58 increase in height towards the transverse central regions thereof as seen in FIG. 2. Thus, the inner surfaces 62 of radiation barrier walls 58 approach each other towards the center regions, but remain spaced from each other even at the region at which they are closest to each other, as seen in FIG. 5A, so that the sub-cavities 26a and 26b remain in communication with each other.

An upwardly facing channel 64 is formed in the upper surface of the region of the free, i.e. the unhinged, long side of cover member 28 and a downwardly facing channel (not shown) is formed in its lower surface. A plurality of longitudinally spaced projections 66 extend from the end surface of the corresponding long side of cover member 30, each projection having a bottom surface 67 which is angled upwardly to the right as viewed in FIG. 2. Referring to FIGS. 1–4 and 6A, a closure slide 68 has a downwardly directed flange 70 formed along its upper edge and a plurality of inwardly directed spaced tabs 72 projecting inwardly from its lower edge. A short upwardly directed lower flange 74 is formed at each end of the closure slide midway between its upper and lower edges, and a handle 76 is fixed to the slide by tabs 77. The closure slide is coupled to the cover member 28 by its upper and lower flanges 70 and 74 being slidingly received in channel 64 and in the downwardly facing channel (not shown). With the closure slide 68 positioned towards the right as viewed (but not shown) in FIG. 1, the tabs 72 are situated so that they will pass through the spaces between the projections 66 of cover member 30 when the cover members are pivoted to close enclosure 12. After the cover members have been pivoted to close enclosure 12, the closure slide 68 is moved to the left as viewed in FIG. 1 to its left-most position, shown in FIG. 1, until the end 68a of closure slide 68 engages an abutment wall 78 formed on the cover member 28. This movement results in the tabs 72 of the slide gradually engaging the bottom surfaces 67 of projections 66 until each tab is tightly engaged with and situated beneath a corresponding projection 66 of cover member 30 to thereby lock the cover members tightly together, i.e., to lock enclosure 12 in its closed condition.

It will be seen from the foregoing that the enclosure 12 constructed in the manner described above including the shield members 52 and 54 received in the respective sub-depressions 36a and 38a defines a first sub-cavity 26a which, upon placing enclosure 12 in a microwave radiation field, is substantially shielded from the radiation, and a second sub-cavity 26b which is not so shielded. In other words, upon subjecting the enclosure 12 to microwave radiation, radiation will pass into the unshielded sub-cavity 26b but will be prevented from passing into the shielded sub-cavity 26a by the shield members 52 and 54. The inner cavity 26 comprising subcavities 26a and 26b are of fixed size and shape being defined by rigid inwardly facing surfaces. For reasons discussed below, a pair of short legs 79 are formed at the left end (as viewed in FIG. 5A) of enclosure 12 so that when the enclosure is placed on a horizontal surface, the shielded sub-cavity 26a will be elevated with respect to the unshielded sub-cavity 26b.

In operation, at least one object 22 to be sterilized is placed within the pouch 16 along with a quantity of liquid 20 whereupon the pouch 16 is sealed to form the gas-tight assembly 14. The enclosure 12 is opened and the gas-tight assembly is placed into the inner cavity 26 thereof. The object or objects 22 to be sterilized are situated in the portion of the pouch interior which is received within the first shielded sub-cavity 26a of enclosure 12 while the liquid 20 is situated in the portion of the pouch 16 which is received within the second unshielded sub-cavity 26b of enclosure 12. In this manner, the shielding means 24 substantially surround a part of the pouch to thereby shield a first interior portion thereof from microwave radiation when the enclosure is placed in a microwave radiation field. In other words, when the gas-tight assembly 14 is situated within enclosure 12 as described above, the shielding means 24 are associated with the pouch 16 to divide the interior thereof into a first interior portion, situated in the shielded sub-cavity 26a, which is substantially free of microwave radiation and a second interior portion, situated in the unshielded sub-cavity 26b, which is exposed to microwave radiation when the enclosure containing the gas-tight assembly is exposed to a microwave radiation field. The shielding means 24 surround at least a part of the pouch to divide the interior thereof into the first shielded interior portion and the second unshielded interior portion.

After the gas-tight assembly 14 has been situated as described above, the enclosure is closed and locked. The marginal edges of the part of the pouch 16 that is situated in the shielded sub-cavity 26a are clamped between the rims 56 of the shield members 52 and 54 while the marginal edges of the part of the pouch that is situated in the unshielded sub-cavity 26b are clamped between shoulders 46 and 50. The enclosure is then placed into the cavity of a microwave generator whereupon it is irradiated. The radiation, designated 90 in FIGS. 5B, 6B and 7B, passes into the unshielded sub-cavity 26b and then into the unshielded interior portion of pouch 16 whereupon the liquid 20 is heated and vaporized.

As the liquid 20 is vaporized, the hot vapor travels into the entire pouch and an overpressure is created within both the shielded and unshielded interior portions of the pouch causing the pouch to expand. Expansion continues until the sheet material 18 of which the pouch 16 is formed presses against the inner surfaces of the shield members 52 and 54 defining the shielded sub-cavity 26a and the inwardly facing surfaces defining the unshielded sub-cavity 26b as seen in FIGS. 5B, 6B and 7B. Engagement of the rigid cavity surfaces by the pouch restricts further expansion of the pouch. This has the beneficial effect of not only assuring that the pouch will not rupture but, additionally, enables the final volume of the expanded pouch to be precisely defined and limited to achieve higher pressures and temperatures in a more precise manner than had been possible heretofore.

As irradiation continues, the object or objects 22 are sterilized under the effect of hot vapor under pressure. The vapor present in the shielded interior portion of the pouch eventually cools and condenses on the inner surface of the pouch. Since the pouch is tilted by legs 79, the condensate will flow into the unshielded portion of the pouch interior where it can be again vaporized by continued irradiation.

Figure 7A:
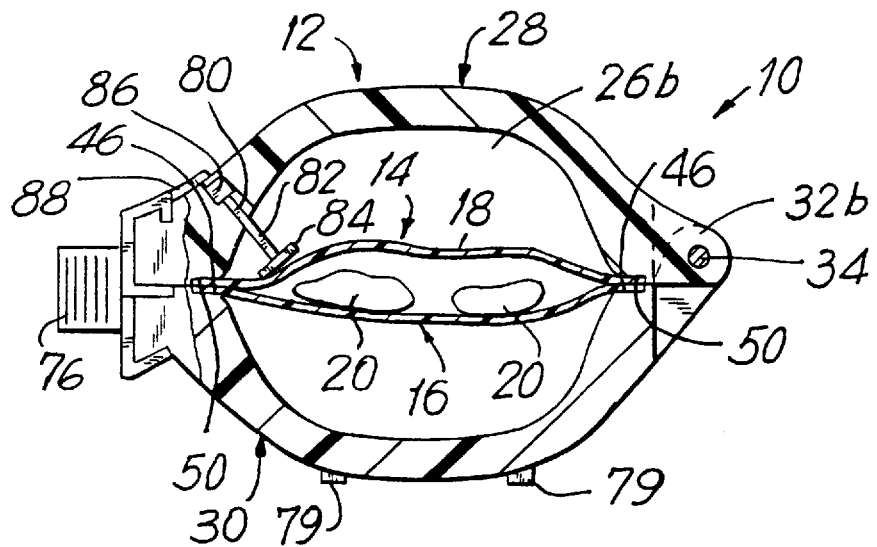
FIG. 7A is a section view taken along line 7—7 of FIG. 1, prior to irradiation.
Figure 7B:
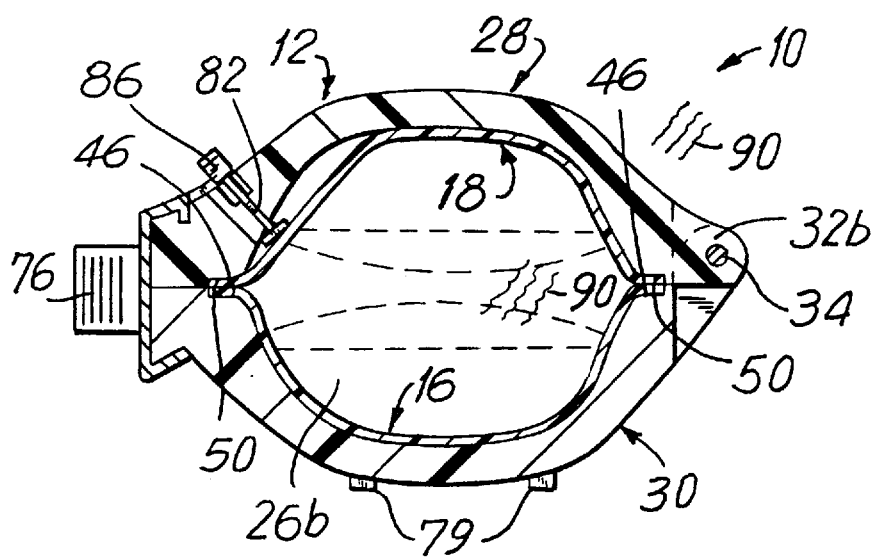
FIG. 7B is a view similar to FIG. 7A, during irradiation.

In accordance with another feature of the invention, referring to FIGS. 1, 2, 4, 7A and 7B, a through bore 80 is formed through the wall of the cover member 28 communicating with the unshielded sub-cavity 26b, and a slide member 82 is received therein. A lug 84 is formed on the inner end of slide member 82 while a detent-indicator 86 is formed on its outer end. Referring to FIGS. 7A and 7B, after the gas-tight assembly 14 has been positioned within the interior cavity of enclosure 12 and the enclosure has been locked by moving the closure slide to its locking position, and prior to initiation of irradiation, the slide member 82 is in an inner position under the force of gravity with the lug 84 engaging the unexpanded pouch 16. In this inner position, the detent-indicator 86 is retracted within the bore 80. Upon irradiation with the consequent vaporization of liquid 20 and expansion of pouch 16 to the configuration illustrated in FIG. 7B, the expanding pouch engages the lug 84 of slide member 82 thereby pushing it outwardly through bore 80 until the detent-indicator 86 reaches the extended position seen in FIG. 7B. The extended condition of the detent-indicator 86 provides a visual indication that the interior of the pouch is at an appropriate over-pressure to achieve effective sterilization of the object contained within pouch 16. Furthermore, as best seen in FIG. 4, the detent-indicator in its extended position is situated in the path of a locking tab 88 formed on the closure slide 68. This prevents the slide 68 from movement towards the right as viewed in FIG. 1 and 4. In this manner, it becomes impossible to unlock the enclosure 12 while the pouch 16 is pressurized, thereby providing another measure of security.

It is seen from the foregoing that the present invention provides an improvement in the methods and apparatus disclosed in applicants' prior patents. The inner cavity 26 of enclosure 12 need not be pressure-tight, since the pressure is maintained within the pouch 16. This enables the enclosure 12 to be constructed in an inexpensive fashion. The provision of the shield means to surround the gas-tight assembly simplifies the shielding of the objects being sterilized from microwave radiation, and the provision of the rigid enclosure cavity enables higher pressures to be achieved in a more precise fashion. All of these benefits are obtained while still retaining the benefits of the basic method and apparatus, namely quick sterilizing cycle time, elimination of the possibility of recontamination, and providing a visual indication that the sterilization process is proceeding. In cases where arcing in a microwave radiation field is not a problem, for example, in certain cases where sharp edges are not present on the object being sterilized, it may be possible to utilize the method and apparatus of the invention without the shielding means which are normally required. In tests that have been conducted, using 10 ml. of water in a bag having a volume of about 50 cc, temperatures of about 295° F. at pressures of 48.3 psig have been obtained in sterilizing objects in times of about two minutes.

Obviously, numerous modifications and variations of the present invention are possible in the light of the above teachings. For example, the shielding means may comprise a metallic coating applied directly to the surfaces defining the sub-depressions 36a and 38a. It is therefore to be understood that within the scope of the claims apended hereto, the invention may be practiced otherwise than as specifically disclosed herein.

What is claimed is:

1. Apparatus for sterilizing at least one object by vapor under pressure, comprising:

a pouch formed of flexible, substantially vapor-impermeable sheet material at least partially transparent to microwave radiation, said pouch being receivable of said at least one object;

liquid receivable within said pouch;

means for irradiating said pouch with microwave electromagnetic radiation to vaporize said liquid to produce an atmosphere of hot vapor under pressure;

shielding means formed of microwave radiation shielding material and adapted to substantially surround at least a part of said pouch for dividing the interior of said pouch into a first interior portion which is substantially shielded from said microwave radiation during irradiation of said pouch by said irradiating means and a second interior portion which is exposed to said microwave radiation during irradiation of said pouch by said irradiating means, said first interior portion being receivable of said at least one object to be sterilized in its substantial entirety and said second interior portion being receivable of said liquid; and means for positioning said shielding means to substantially surround at least part of said pouch to shield said first interior portion thereof, said shielding positioning means comprising an enclosure having a substantially closed interior cavity for receiving said pouch in its substantial entirety;

whereby upon irradiating said pouch with microwave radiation, said at least one object situated in said first interior portion of said pouch is substantially entirely shielded from said radiation, and said liquid situated in said second interior portion is exposed to said radiation whereupon it is heated and then vaporized thereby, whereupon said at least one object is sterilized under the effect of vapor under pressure.

2. Apparatus as recited in claim 1 wherein said shielding means comprise at least one shield member.

3. Apparatus as recited in claim 2 wherein said shielding means comprise a pair of shield members.

4. Apparatus as recited in claim 1 wherein said enclosure comprises means for holding said pouch in said interior cavity.

5. Apparatus as recited in claim 4 wherein said shielding means comprise at least one shield member, and said enclosure further comprises means for holding said at least one shield member to surround at least a part of said pouch to shield said first interior portion thereof.

6. Apparatus as recited in claim 1 wherein said liquid comprises water.

7. Apparatus as recited in claim 1 wherein said liquid comprises hydrogen peroxide.

8. Apparatus as recited in claim 1 further including means for elevating said first interior portion of said pouch with respect to said second interior portion of said pouch.

9. Apparatus for sterilizing at least one object by vapor under pressure, comprising:

a pouch formed of flexible, substantially vapor-impermeable sheet material at least partially transparent to microwave radiation, said pouch being receivable of said at least one object;

liquid receivable within said pouch;

means for irradiating said pouch with microwave electromagnetic radiation to vaporize said liquid to produce an atmosphere of hot vapor under pressure;

shielding means formed of microwave radiation shielding material and adapted to substantially surround at least a part of said pouch for dividing the interior of said pouch into a first interior portion which is substantially shielded from said microwave radiation during irradiation of said pouch by said irradiating means and a second interior portion which is exposed to said microwave radiation during irradiation of said pouch by said irradiating means, said first interior portion being receivable of said at least one object to be sterilized in its substantial entirety and said second interior portion being receivable of said liquid; and means for positioning said shielding means to substantially surround at least part of said pouch to shield said first interior portion thereof, said shielding positioning means comprising a pair of cover members operatively associated with each other and defining a substantially closed interior space between them, and means for holding said pouch in its substantial entirety in said interior space;

whereby upon irradiating said pouch with microwave radiation, said at least one object situated in said first interior portion of said pouch is substantially entirely shielded from said radiation, and said liquid situated in said second interior portion is exposed to said radiation whereupon it is heated and then vaporized thereby, whereupon said at least one object is sterilized under the effect of vapor under pressure.

10. Apparatus as recited in claim 9 wherein said shielding means comprise a pair of shield members, and said shielding means positioning means further comprise means for holding each of said shield members on a respective one of said cover members so that when said cover members are operatively associated with each other said shield members define an interior subspace between them to substantially surround said first interior portion of said pouch.

11. Apparatus as recited in claim 10 wherein each of said shield members has a substantially concave configuration.

12. Apparatus for sterilizing at least one object by vapor under pressure, comprising:
a pouch formed of flexible substantially vapor-impermeable sheet material at least partially transparent to microwave electromagnetic radiation, said pouch having a sealable opening through which said at least one object can be introduced into the interior thereof;
liquid receivable within said pouch;
means for irradiating said pouch with microwave radiation to vaporize said liquid to produce an atmosphere of hot vapor under pressure;
shielding means comprising at least one shield member formed of microwave electromagnetic radiation shield material and having inwardly facing rigid surface means defining a shielded space in which at least a part of said pouch is situated to define a first interior pouch portion which is substantially free of said microwave radiation during irradiation of said pouch by said irradiating means and a second interior pouch portion which is exposed to said microwave radiation during irradiation of said pouch by said irradiating means, said first interior portion being receivable of said at least one object to be sterilized in its substantial entirety and said second interior portion being receivable of said liquid; and
said pouch and inwardly facing surface means of said at least one shield member being formed and positioned so that upon irradiating said pouch and vaporizing said liquid, an overpressure is created within said pouch which causes said pouch to expand until said sheet material thereof presses against said inwardly facing surface means of said at least one shield member under pressure;
whereby upon irradiating said pouch with microwave radiation, said at least one object situated in said first interior portion of said pouch is substantially entirely shielded from said radiation, and said liquid situated in said second interior portion is exposed to said radiation whereupon it is heated and then vaporized thereby, whereupon said at least one object is sterilized under the effect of vapor under pressure.

13. Apparatus as recited in claim 12 further including means for holding said at least one shield member and pouch such that said at least one shield member defines said shielded space and divides the interior of said pouch into said first and second interior portions.

14. Apparatus as recited in claim 12 further including enclosure means for defining an interior cavity and for holding said pouch in said cavity and positioning said at least one shield member to define said shielded space to divide the interior of said pouch into said first and second interior portions, and so that said sheet material of said pouch presses against said inwardly facing surface means of said at least one shield member upon expansion of said pouch during irradiation.

15. Apparatus as recited in claim 14 wherein said enclosure means comprise a housing including a pair of cover members operatively associated with each other, means provided on said cover members for holding said pouch and positioning said at least one shield member.

16. Apparatus as recited in claim 15 wherein said shielding means comprise a pair of shield members, and wherein each of said shield members is fixed to a respective one of said cover members.

17. Apparatus as recited in claim 16 wherein each of said shield members is substantially concave.

18. Apparatus for sterilizing at least one object by vapor under pressure, comprising:
a pouch formed of flexible substantially vapor-impermeable sheet material at least partially transparent to microwave electromagnetic radiation, said pouch having a sealable opening through which said at least one object can be introduced into the interior thereof;
liquid receivable within said pouch;
means for irradiating said pouch with microwave radiation to vaporize said liquid to produce an atmosphere of hot vapor under pressure;
shielding means comprising at least one shield member formed of microwave electromagnetic radiation shield material defining a shielded space in which at least a part of said pouch is situated to define a first interior pouch portion which is substantially free of said microwave radiation during irradiation of said pouch by said irradiating means and a second interior pouch portion which is exposed to said microwave radiation during irradiation of said pouch by said irradiating means, said first interior portion being receivable of said at least one object to be sterilized in its substantial entirety and said second interior portion being receivable of said liquid; and
enclosure means for defining a substantially closed interior cavity and for holding said pouch in its substantial entirety in said cavity and positioning said at least one shield member to divide the interior of said pouch into said first and second interior portions;
whereby upon irradiating said pouch with microwave radiation, said at least one object situated in said first interior portion of said pouch is substantially entirely shielded from said radiation, and said liquid situated in said second interior portion is exposed to said radiation whereupon it is heated and then vaporized thereby, whereupon said at least one object is sterilized under the effect of vapor under pressure.

19. Apparatus as recited in claim 18 wherein said at least one shield member includes inwardly facing, substantially rigid surface means defining said shielded space, and wherein upon irradiating said pouch and vaporizing said liquid, an overpressure is created within said pouch which causes said pouch to expand such that said sheet material thereof presses against said inwardly facing surface means of said at least one shield member.

20. Apparatus as recited in claim 18 further including means for providing an indication visible from the exterior of said enclosure means that said pouch has expanded under pressure.

21. Apparatus as recited in claim 20 wherein said indication means comprise a member movably mounted on said enclosure means and adapted to be engaged by said sheet material of said pouch as said pouch expands under pressure.

22. Apparatus as recited in claim 18 further including means for locking said enclosure means to prevent access to said interior cavity when said pouch has expanded under pressure.

23. Apparatus as recited in claim 22 wherein said locking means comprises a member movably mounted on said enclosure means and adapted to be engaged by said sheet material of said pouch as said pouch expands under pressure.

24. Apparatus for sterilizing at least one object by vapor under pressure, comprising:
    a pouch formed of flexible substantially vapor-impermeable sheet material at least partially transparent to microwave radiation, said pouch being receivable of said at least one object;
    liquid receivable within said pouch;
    means for irradiating said pouch with microwave radiation to vaporize said liquid to produce an atmosphere of hot vapor under pressure; and
    enclosure means formed of microwave radiation transparent material having inwardly facing substantially rigid surfaces defining an interior cavity, said enclosure means including means for holding said pouch in said cavity, and wherein upon irradiating said pouch with microwave radiation, said liquid receivable within said pouch is exposed to said radiation whereupon it is heated and then vaporized thereby, whereupon an overpressure is created within said pouch which causes said pouch to expand until said sheet material thereof presses against said inwardly facing surfaces of said enclosure means defining said interior cavity, to thereby prevent further expansion of said pouch.

25. Apparatus as recited in claim 24 further including shielding means associated with said pouch for dividing the interior of said pouch into a first interior portion which is substantially free of said microwave radiation during irradiation of said pouch by said irradiating means and a second interior portion which is exposed to said microwave radiation during irradiation of said pouch by said irradiating means, said first interior portion being receivable of said at least one object to be sterilized and said second interior portion being receivable of said liquid.

26. Apparatus as recited in claim 25 wherein said shielding means is associated with said enclosure means and substantially surrounds at least part of said pouch to shield said first interior portion thereof from said microwave radiation during irradiation of said pouch by said irradiating means.

27. Apparatus as recited in claim 26 wherein said shielding means comprise at least one shield member associated with said enclosure means, said at least one shield member having inwardly facing surfaces comprising at least in part said inwardly facing surfaces of said enclosure means which define said interior cavity.

28. Apparatus as recited in claim 27 wherein said shielding means comprise a pair of substantially concave shield members having end portions which cooperate to substantially divide said first and second interior pouch portions from each other.

* * * * *